US010201180B2

United States Patent
Kobal et al.

(10) Patent No.: US 10,201,180 B2
(45) Date of Patent: Feb. 12, 2019

(54) INHIBITION OF UNDESIRED SENSORY EFFECTS BY THE COMPOUND CAMPHOR

(71) Applicant: Philip Morris USA Inc., Richmond, VA (US)

(72) Inventors: Gerd Kobal, Sandy Hook, VA (US); Prasad Polur, Woodbridge, VA (US); Maria Gogova, Richmond, VA (US); Diana McKinney, Midlothian, VA (US)

(73) Assignee: Philips Morris USA Inc., Richmond, VA (US)

( * ) Notice: Subject to any disclaimer, the term of this patent is extended or adjusted under 35 U.S.C. 154(b) by 0 days.

(21) Appl. No.: 14/591,485

(22) Filed: Jan. 7, 2015

(65) Prior Publication Data

US 2015/0126561 A1 May 7, 2015

Related U.S. Application Data

(62) Division of application No. 13/071,889, filed on Mar. 25, 2011, now Pat. No. 8,952,038.

(Continued)

(51) Int. Cl.
| | |
|---|---|
| *A61K 31/435* | (2006.01) |
| *A24B 15/10* | (2006.01) |
| *A24B 15/30* | (2006.01) |
| *A61K 9/00* | (2006.01) |
| *A61K 31/125* | (2006.01) |
| *A61K 31/465* | (2006.01) |
| *A61K 47/08* | (2006.01) |
| *A24B 13/00* | (2006.01) |
| *A24B 15/18* | (2006.01) |

(Continued)

(52) U.S. Cl.
CPC .............. *A24B 15/10* (2013.01); *A24B 13/00* (2013.01); *A24B 15/186* (2013.01); *A24B 15/30* (2013.01); *A24B 15/345* (2013.01); *A61K 9/009* (2013.01); *A61K 9/0058* (2013.01); *A61K 31/125* (2013.01); *A61K 31/465* (2013.01); *A61K 47/08* (2013.01)

(58) Field of Classification Search
CPC ......... A24B 15/30; A24B 13/00; A24B 15/10; A24B 15/345; A24B 15/186; A61K 9/009; A61K 31/125; A61K 31/465; A61K 9/0058; A61K 47/08; A61K 2300/00
See application file for complete search history.

(56) References Cited

U.S. PATENT DOCUMENTS

| | | |
|---|---|---|
| 4,351,347 A | 9/1982 | Sprecker |
| 4,378,380 A | 3/1983 | Scarpellino et al. |

(Continued)

FOREIGN PATENT DOCUMENTS

WO    WO 99/39595    8/1999

OTHER PUBLICATIONS

Official Action dated Apr. 15, 2015 for Russian Patent Appln. No. 2012145537.

(Continued)

*Primary Examiner* — Lezah Roberts
(74) *Attorney, Agent, or Firm* — Buchanan Ingersoll & Rooney LLC

(57) ABSTRACT

A smokeless tobacco product or medicinal nicotine product includes nicotine and camphor dissolved in a non-flavored oily carrier. Preferably, the camphor is present in a concentration ranging from about 600 ppm to about 1300 ppm. Also disclosed are methods of making such products.

4 Claims, 12 Drawing Sheets

Related U.S. Application Data

(60) Provisional application No. 61/318,253, filed on Mar. 26, 2010.

(51) Int. Cl.
*A24B 15/34* (2006.01)
*A61K 9/68* (2006.01)

(56) References Cited

U.S. PATENT DOCUMENTS

| | | | |
|---|---|---|---|
| 4,959,380 A | 9/1990 | Wilson | |
| 5,167,244 A | 12/1992 | Kjerstad | |
| 5,298,257 A | 3/1994 | Bannon et al. | |
| 5,456,745 A | 10/1995 | Roreger et al. | |
| 5,505,958 A | 4/1996 | Bello et al. | |
| 5,556,636 A | 9/1996 | Yano et al. | |
| 5,643,905 A | 7/1997 | Moormann | |
| 5,770,220 A | 6/1998 | Meconi et al. | |
| 5,891,463 A | 4/1999 | Bello et al. | |
| 6,019,851 A | 2/2000 | Pittet et al. | |
| 6,103,266 A | 8/2000 | Tapolsky et al. | |
| 6,150,424 A | 11/2000 | Breitenbach et al. | |
| 6,165,512 A | 12/2000 | Mezaache et al. | |
| 6,183,770 B1 | 2/2001 | Muchin et al. | |
| 6,224,900 B1 | 5/2001 | Hoffmann | |
| 6,264,977 B1 | 7/2001 | Hoffmann | |
| 6,270,804 B1 | 8/2001 | Getz et al. | |
| 6,277,401 B1 | 8/2001 | Bello et al. | |
| 6,284,803 B1 | 9/2001 | Kothrade et al. | |
| RE37,934 E | 12/2002 | Hoffmann | |
| 6,548,510 B1 | 4/2003 | Asmussen et al. | |
| 6,562,363 B1 | 5/2003 | Mantelle et al. | |
| 6,582,724 B2 | 6/2003 | Hsu et al. | |
| 6,627,234 B1 | 9/2003 | Johnson et al. | |
| 6,638,528 B1 | 10/2003 | Kanios | |
| 6,668,839 B2 | 12/2003 | Williams | |
| 6,682,757 B1 | 1/2004 | Wright | |
| 6,750,291 B2 | 6/2004 | Kim et al. | |
| 6,756,052 B1 | 6/2004 | Koch et al. | |
| 6,780,504 B2 | 8/2004 | Rupprecht et al. | |
| 6,789,546 B2 | 9/2004 | Reznick et al. | |
| 6,845,777 B2 | 1/2005 | Pera | |
| 6,854,470 B1 | 2/2005 | Pu | |
| 6,893,655 B2 | 5/2005 | Flanigan et al. | |
| 6,893,661 B1 | 5/2005 | Odidi et al. | |
| 6,936,268 B1 | 8/2005 | Muta et al. | |
| 6,949,264 B1 | 9/2005 | McGrew et al. | |
| 6,953,593 B2 | 10/2005 | Kuhrts | |
| 7,008,628 B2 | 3/2006 | Ron et al. | |
| 7,063,859 B1 | 6/2006 | Kanios et al. | |
| 7,163,705 B2 | 1/2007 | Johnson et al. | |
| 7,176,183 B2 | 2/2007 | Rodgers et al. | |
| 7,186,958 B1 | 3/2007 | Nelson | |
| 7,534,454 B2 | 5/2009 | Karerat et al. | |
| 7,625,924 B2 | 12/2009 | Nguyen et al. | |
| 7,754,236 B2 | 7/2010 | Suzuki et al. | |
| 7,923,585 B2 | 4/2011 | Ishida et al. | |
| 7,980,251 B2 | 7/2011 | Winterson et al. | |
| 7,988,991 B2 | 8/2011 | Tateishi et al. | |
| 7,988,997 B2 | 8/2011 | Von Falkenhausen et al. | |
| 8,017,146 B2 | 9/2011 | Stefano et al. | |
| 8,226,931 B2 | 7/2012 | Kindel et al. | |
| 8,312,886 B2 | 11/2012 | Mishra et al. | |
| 8,469,037 B2 | 6/2013 | Liu et al. | |
| 8,616,221 B2 | 12/2013 | Torrence et al. | |
| 8,691,267 B2 | 4/2014 | Terahara et al. | |
| 8,846,075 B2 | 9/2014 | Jonsson et al. | |
| 8,901,024 B2 | 12/2014 | Trancik et al. | |
| 8,952,038 B2 | 2/2015 | Kobal et al. | |
| 2002/0004065 A1 | 1/2002 | Kanios | |
| 2002/0017295 A1 | 2/2002 | Weers et al. | |
| 2004/0022836 A1 | 2/2004 | Degen et al. | |
| 2004/0033255 A1 | 2/2004 | Baker et al. | |
| 2004/0156886 A1 | 8/2004 | Kose | |
| 2004/0202708 A1 | 10/2004 | Roehrig et al. | |
| 2004/0219198 A1 | 11/2004 | Johnson et al. | |
| 2004/0224012 A1 | 11/2004 | Suvanprakorn et al. | |
| 2004/0258753 A1 | 12/2004 | Demeester et al. | |
| 2005/0084459 A1 | 4/2005 | Reznick et al. | |
| 2005/0118246 A1 | 6/2005 | Wong et al. | |
| 2005/0136112 A1 | 6/2005 | Gonzales et al. | |
| 2005/0241658 A1 | 11/2005 | Pera | |
| 2006/0078604 A1 | 4/2006 | Kanios et al. | |
| 2006/0110415 A1 | 5/2006 | Gupta | |
| 2006/0110449 A1 | 5/2006 | Lorber et al. | |
| 2006/0141031 A1 | 6/2006 | Nelson et al. | |
| 2006/0188554 A1 | 8/2006 | Nakashima et al. | |
| 2006/0228418 A1 | 10/2006 | Mitchell | |
| 2006/0243290 A1 | 11/2006 | Reich et al. | |
| 2007/0026025 A1 | 2/2007 | Mitchell | |
| 2007/0062548 A1 | 3/2007 | Horstmann et al. | |
| 2007/0074733 A1 | 4/2007 | Rasouli et al. | |
| 2007/0125765 A1 | 6/2007 | Nelson | |
| 2007/0261707 A1 | 11/2007 | Winterson et al. | |
| 2008/0063748 A1 | 3/2008 | Massey et al. | |
| 2008/0102157 A1 | 5/2008 | Hofacker et al. | |
| 2008/0131467 A1 | 6/2008 | Nelson et al. | |
| 2008/0202533 A1 | 8/2008 | Mishra et al. | |
| 2008/0299249 A1 | 12/2008 | Hirt et al. | |
| 2009/0032040 A1 | 2/2009 | Luzenberg, Jr. | |
| 2009/0175982 A1 | 7/2009 | Boghani et al. | |
| 2010/0018883 A1 | 1/2010 | Patel | |
| 2010/0061940 A1 | 3/2010 | Axelsson et al. | |

OTHER PUBLICATIONS

Craven, R., Ions Channels: The Comfort of Camphor, Nature Review Neuroscience, 6, p. 826 (1-3), Nov. 2005.

L. Liu et al., "Nicotine Inhibits Voltage-Dependent Sodium Channels and Sensitizes Vanilloid Receptors," J. Neurophysiol. 91: 1482-91, The American Physiological Society (2004).

Kichko et al., "Irritant? Included CGRP Release from the Isolated Mouse Trachea and Role of TRP Channels," Acta Physiologica 2007; vol. 189, Supplement 653 :P20-L1-03 (2007).

Park et al., "Noncompetitive Inhibition by Camphor of Nicotinic Acetylcholine Receptors," Biochem Pharmacol. 61 (2001) 787-793.

Bautista et al., 102 Proc. Natl. Acad. Sci U.S.A. 12248-52 (2005).

Salazar et al., 11 Nat. Neurosci. 255-61 (2008).

Hinman et al., 103 Proc. Natl. Acad. Sci U.S.A. 19564-68 (2006).

Susankova et al., 70 Mol. Pharmacol. 383-94 (2006).

International Search Report for International Application No. PCT/IB2011/000944 dated Mar. 26, 2012.

Hillis et al., "Polyphenols in the Leaves of Eucalyptus L'Herit: A Chemotaxonomic Survey—I," Phytochemistry, vol. 5, No. 6, 1075-1090 (Nov. 1966).

Database WPI, Thomson Scientific, London, GB, AN 2005-372696 XP000002658810, & CN 1 579 258 A (Wang Ziyong) Feb. 16, 2005.

Written Opinion of the International Searching Authority, dated Oct. 11, 2012, of PCT/IB2011/000994 filed Mar. 28, 2011.

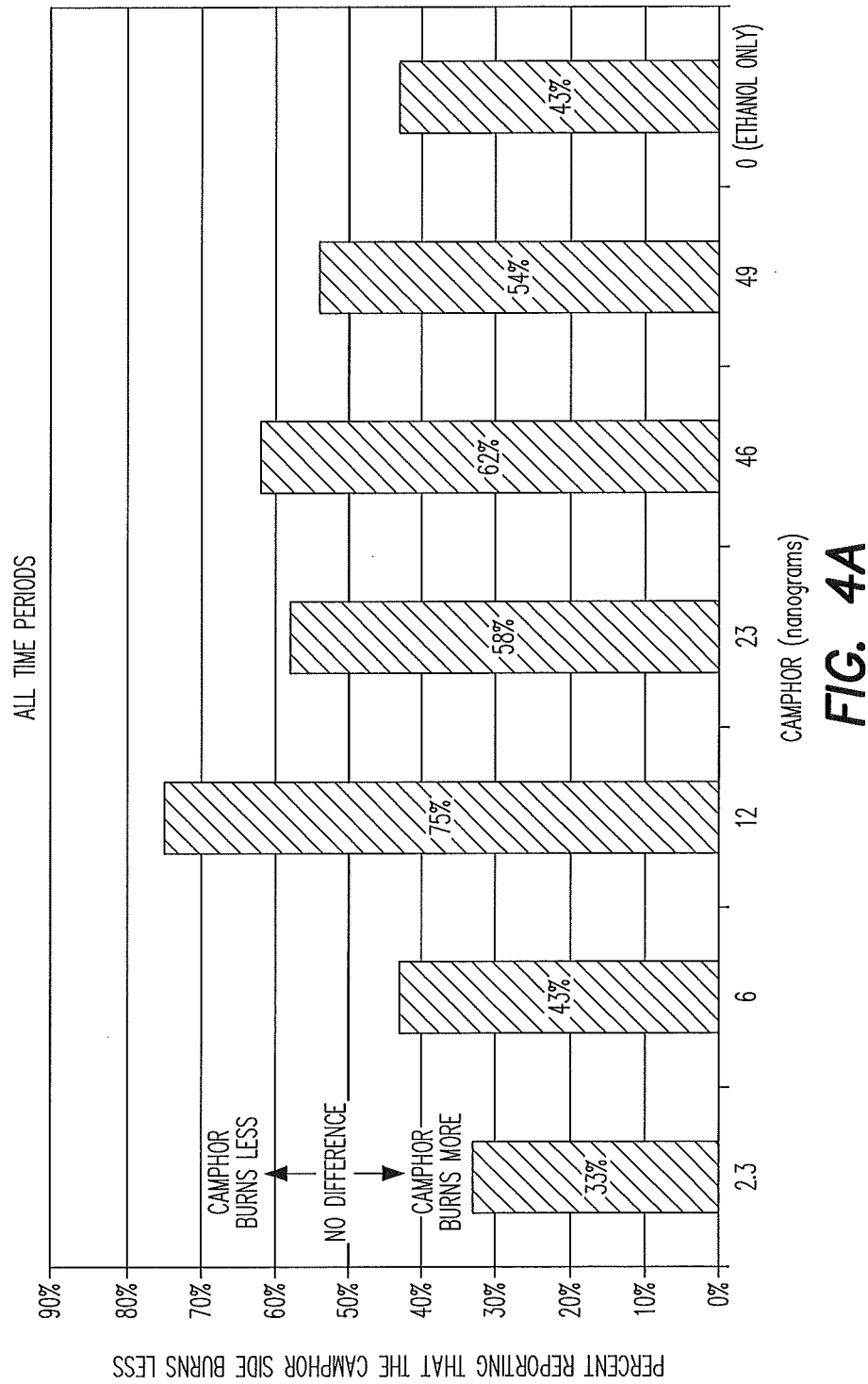

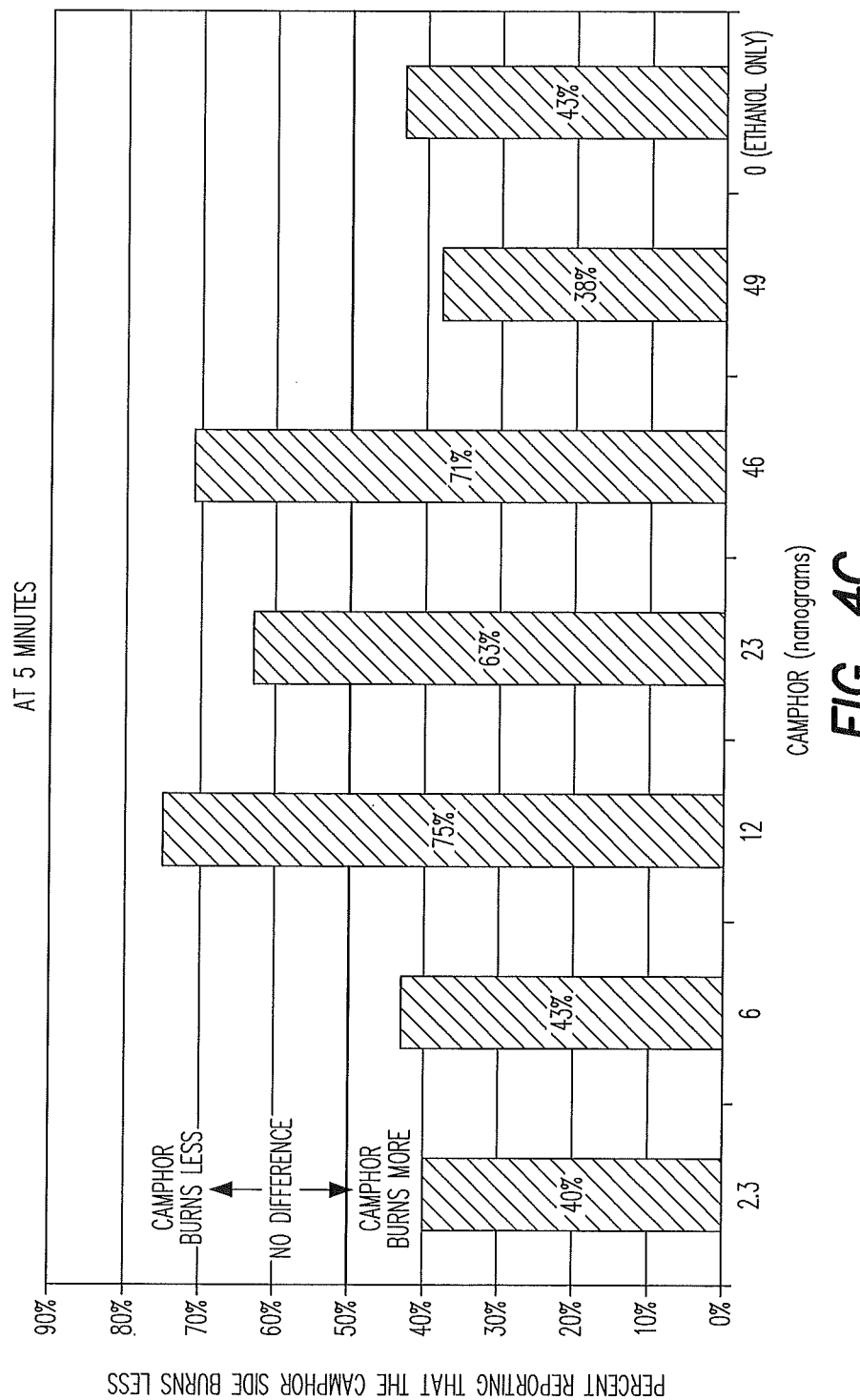

INHIBITION OF UNDESIRED SENSORY EFFECTS BY THE COMPOUND CAMPHOR

CROSS REFERENCE TO RELATED APPLICATION

This application is a divisional application of U.S. patent application Ser. No. 13/071,889, filed Mar. 25, 2011, entitled INHIBITION OF UNDESIRED SENSORY EFFECTS BY THE COMPOUND CAMPHOR which claims priority under 35 U.S.C. § 119(e) to U.S. Provisional Application No. 61/318,253, filed on Mar. 26, 2010, the entire content of each is incorporated herein by reference thereto.

SUMMARY

In an embodiment, smokeless tobacco product or medicinal nicotine product, comprises nicotine, and camphor dissolved in a non-flavored oily carrier.

In another embodiment, a method of making a smokeless tobacco product or medicinal nicotine product, comprises combining nicotine and camphor dissolved in a non-flavored oily carrier.

An additional embodiment the camphor is present in a concentration ranging from about 600 to about 1300 ppm.

BRIEF DESCRIPTION OF THE DRAWINGS

FIGS. 4A and 4B show results of a study to determine whether camphor affected perceived irritation in the mouth from use of snus in adult smokers who are novice oral tobacco users, with the camphor delivered from an ethanol and water solution. FIG. 4A shows combined results from all time periods, and FIGS. 4B, 4C, and 4D show results at two, five, and ten minutes, respectively.

FIG. 5 contains illustrations of exemplary oral pouch products as described herein.

DETAILED DESCRIPTION

Figure 1A:
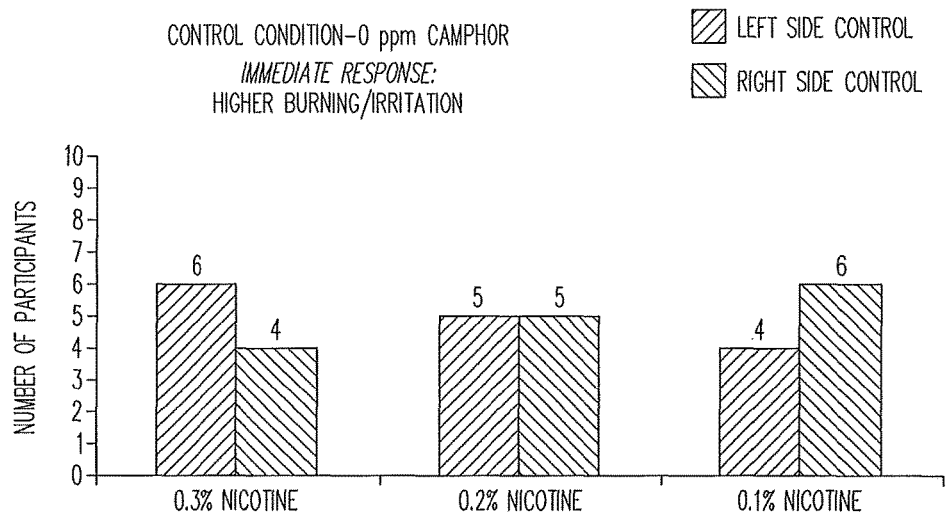
FIGS. 1A, 1B, 1C, and 1D show results on the effect of pre-treatment with camphor on immediately-perceived sensory irritation from nicotine with 0 ppm, 25 ppm, 50 ppm, or 100 ppm, respectively, of camphor from an ethanol/water solution and delivered on a strip.
Figure 1B:
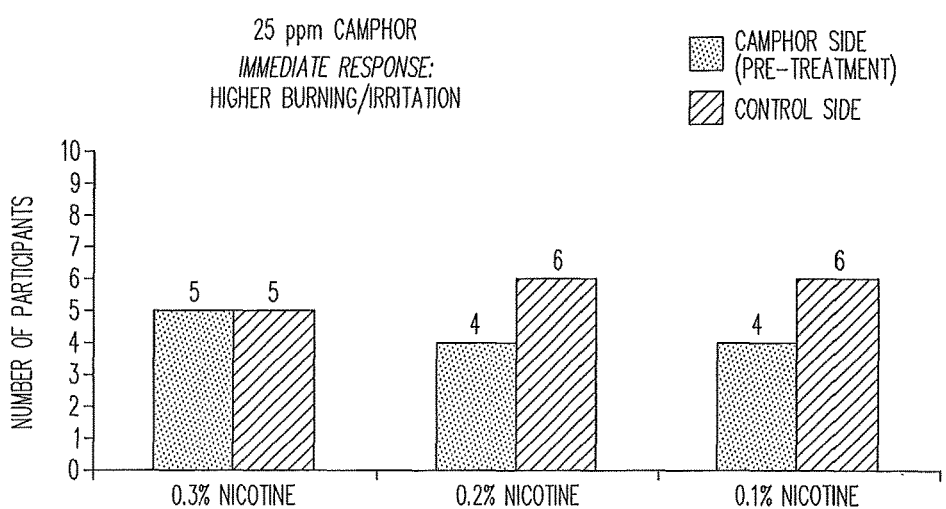
Figure 1C:
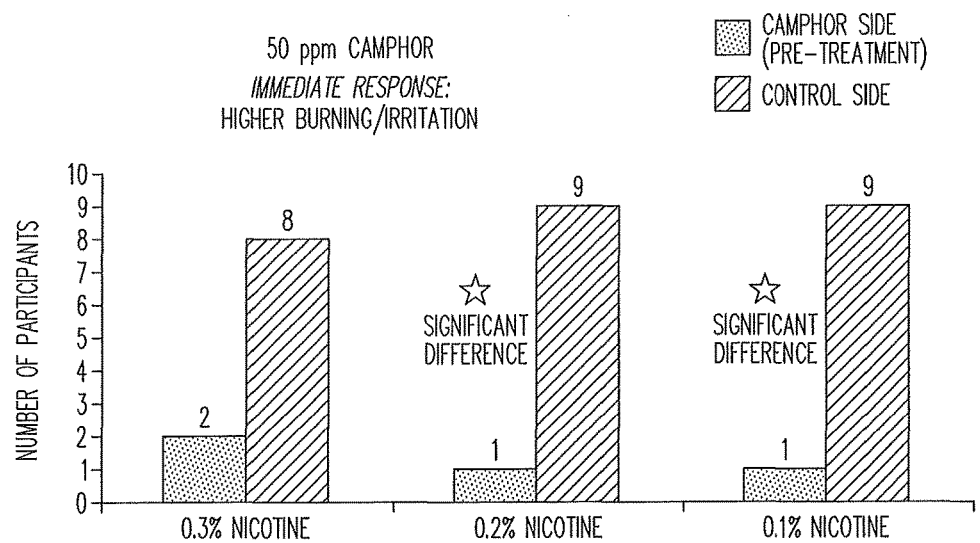
Figure 1D:
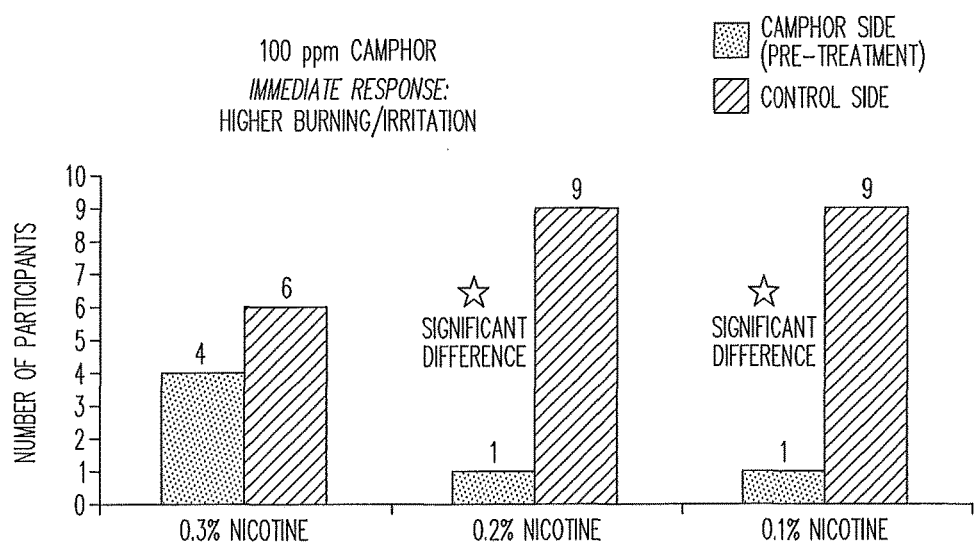
Figure 2A:
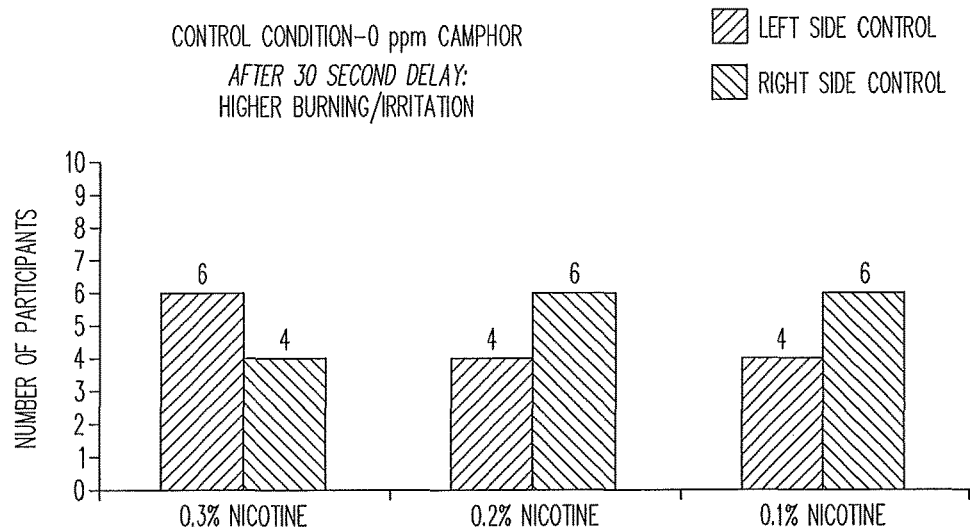
FIGS. 2A, 2B, 2C, and 2D show results on the effect of pre-treatment with camphor on sensory irritation from nicotine after 30 seconds, using 0 ppm, 25 ppm, 50 ppm, or 100 ppm, respectively, of camphor from an ethanol/water solution and delivered on a strip.
Figure 2B:
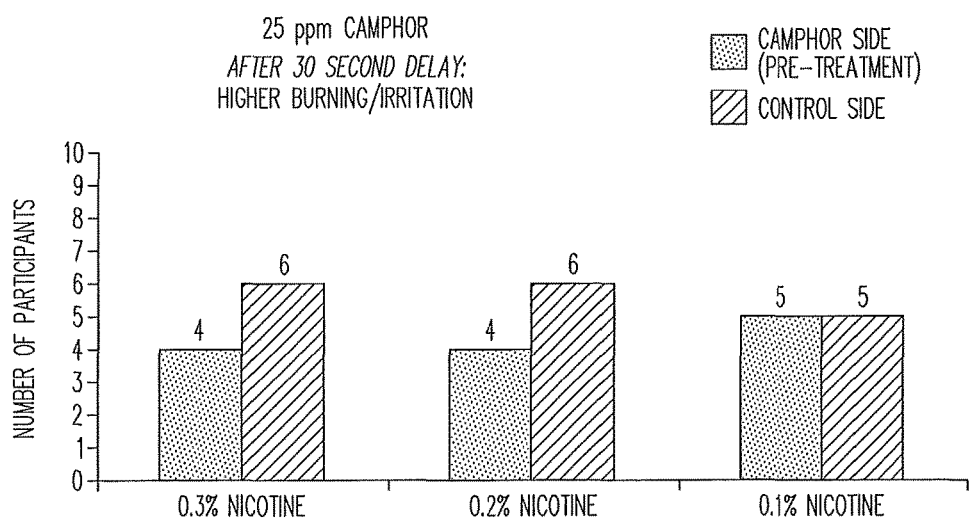
Figure 2C:
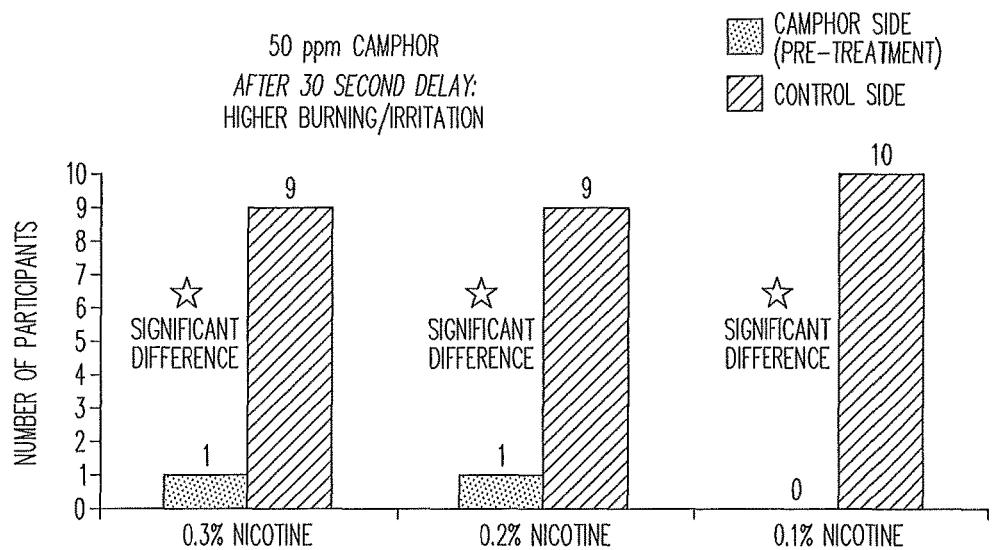
Figure 2D:
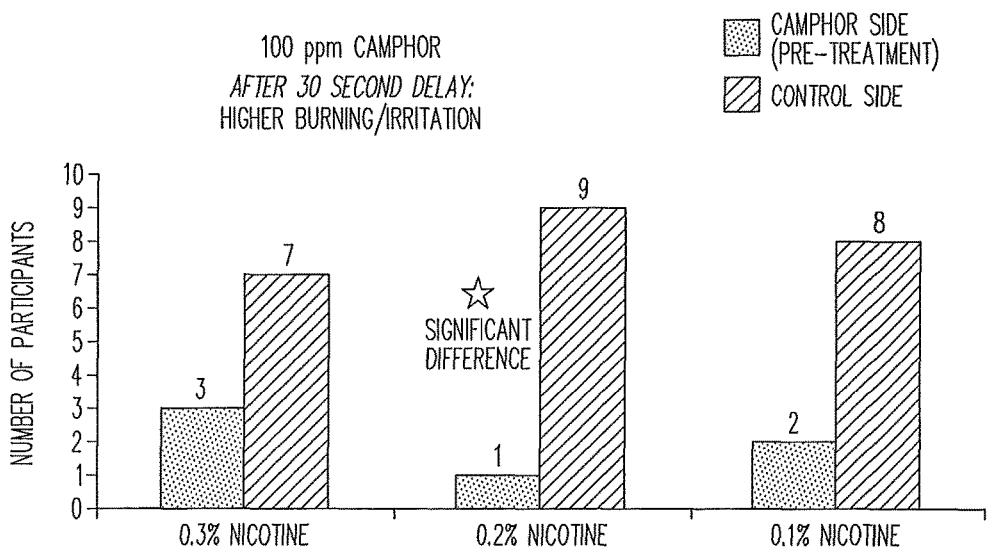
Figure 3A:
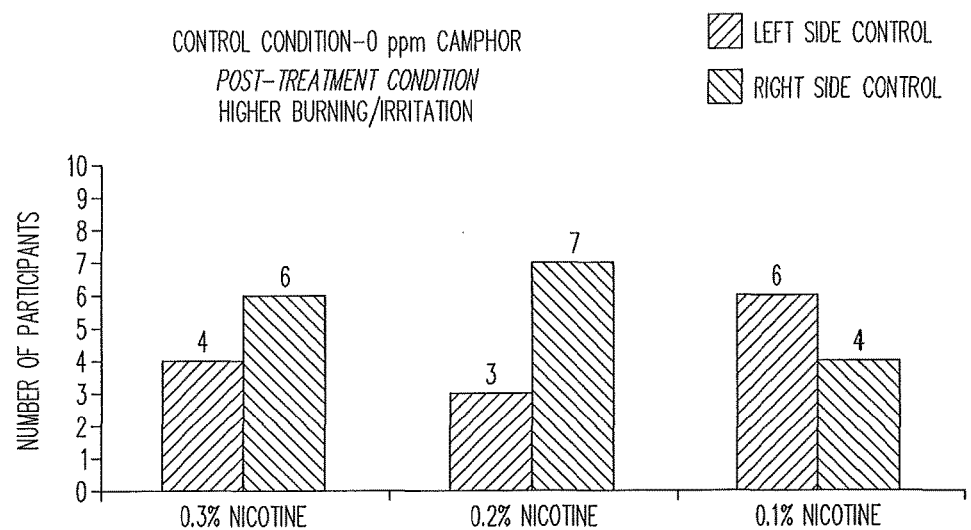
FIGS. 3A, 3B, 3C, and 3D show results on the effect of post-treatment with camphor on sensory irritation from nicotine using 0 ppm, 25 ppm, 50 ppm, or 100 ppm, respectively, of camphor from an ethanol/water solution and delivered on a strip.
Figure 3B:
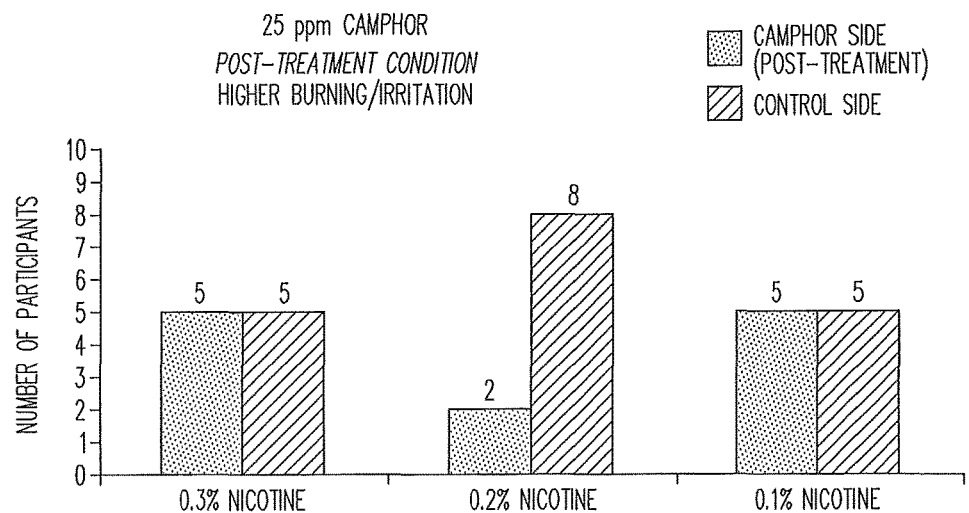
Figure 3C:
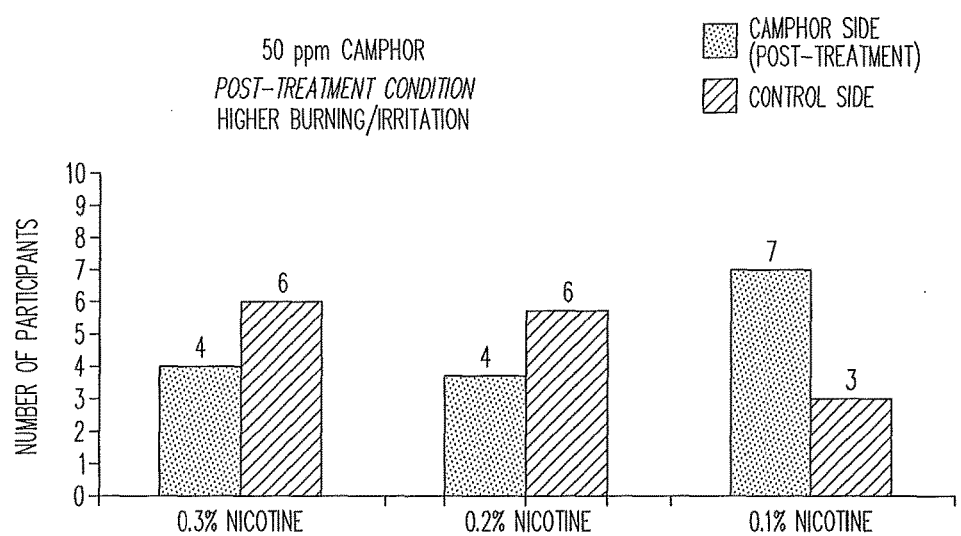
Figure 3D:
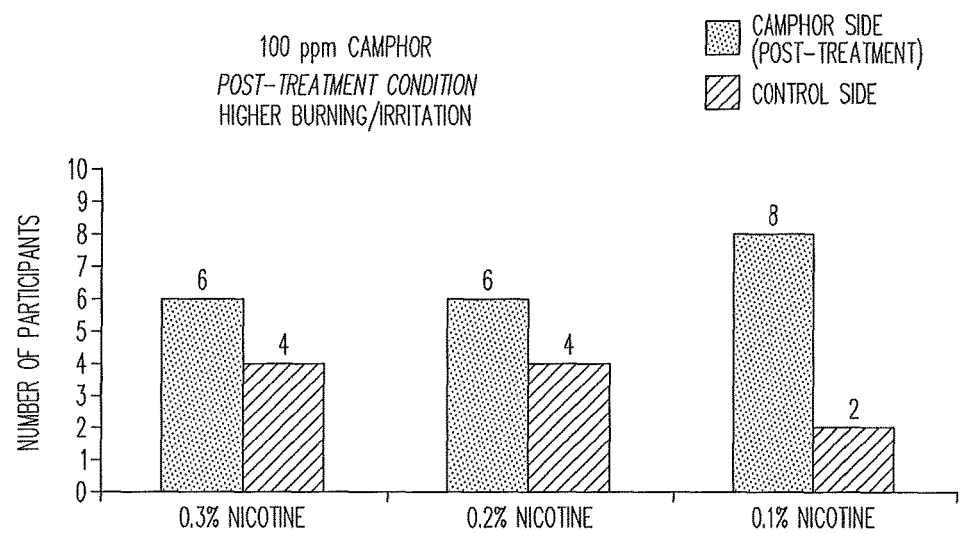

As used herein, when it is said that a material does not exhibit a sensory effect, it means that an average consumer cannot detect a taste or other sensation (for example, burning, tingling, and/or cooling) arising from the material when using a portion of the product.

The term "edible" as used herein denotes the ability of a material or product to be enjoyed and at least partially consumed via the mouth. It includes products such as pouched tobacco wherein the product is not intended to be consumed in its entirety.

As used herein, the term "portion" denotes an amount of a product that would typically be used by a consumer as an individual serving and/or dose. For example, a portion refers to a single lozenge and/or a single puff from an inhaler.

The term "non-flavored oily carrier" and the like refers to a hydrophobic carrier substantially lacking in flavor, and excludes essential oils such as peppermint oil and the like. Unless otherwise described, it includes hydrophobic materials that are solid at room temperature, such as waxes.

The term "about" when used in conjunction with a stated numerical value or range denotes somewhat more or somewhat less than the stated value or range, to within a range of ±10% of that stated.

Camphor and Sensory Irritation

Nicotinic acetylcholine receptors are located on a variety of nerve endings in the peripheral nervous system and play a role in transmission of sensations of irritation (e.g. burning) to the brain. Nicotine, found in tobacco, can activate these receptors.

It has been reported that camphor can effectively inhibit activation of nerve fibers induced by the nicotinic agonist nicotine in an isolated mouse trachea model. Kichko et al., Acta Physiologica 2007; Volume 189, Supplement 653:P20-L1-03. Camphor has also been reported to inhibit norepinephrine release from adrenal gland cells by inhibiting acetylcholine receptors. Park et al., Biochem. Pharmacol. 2002; 61(7):787-793.

Activation of nerves by nicotine can lead to sensations, varying with, e.g., the location of these fibers in the gastrointestinal tract. For example, activation in the mouth can result in burning sensations, activation in the esophagus tends to result in a burning sensation and a bolus feel or in other instances hiccups and/or nausea, activation in the stomach would result in an urge to burp, etc.

Camphor Reduced Sensory Irritation from Nicotine

FIGS. 1 and 2 show the results of a study on the effect of pre-treatment with camphor on sensory irritation from nicotine. Camphor was applied to tongues of human volunteers prior to application of a nicotine solution. Randomized sides of tongues were selected for application of 20 microliters of 0 ppm, 25 ppm, 50 ppm, or 100 ppm of camphor from an ethanol/water solution on a strip (thus, about 0, 500, 1000, or 2000 picograms, respectively) for 30 seconds. Then, the subjects sipped, rinsed, then spit 0.1%, 0.2%, or 0.3% of a nicotine solution for a 5 second application. Participants were then asked which side of the tongue has the strongest burning sensation. Responses were collected both immediately (within 5 seconds) (FIG. 1) and after 30 seconds (FIG. 2). Controls received no camphor, and a baseline was established at zero camphor.

FIG. 3 shows results of a study on the effect of post-treatment with camphor on sensory irritation from nicotine. The study was generally conducted as described above for pre-treatment with camphor, however in this instance the nicotine was provided 30 seconds before the camphor or zero-camphor control. Randomized sides of tongues were selected for application of 20 microliters of 0 ppm, 25 ppm, 50 ppm, or 100 ppm of camphor on a strip (thus, about 0, 500, 1000, or 2000 picograms, respectively) for 30 seconds.

It can be seen from these data that the pre-treatment with camphor significantly reduced perceived burning from nicotine, both immediately and 30 seconds after initial exposure.

Preferably, the camphor is present in a quantity so that it does not exhibit a sensory effect by itself (for example, excessive cooling, detectable smell, and/or taste). Alternately, the product may be formulated so as to take advantage of inherent organoleptic properties of the camphor.

Threshold of Irritation from Camphor

A further study was conducted to determine the threshold at which camphor itself would cause sensory irritation.

Each test used two milliliters (2 ml) of a camphor solution. The camphor was dissolved in ethanol and further diluted in water. Participants received sequentially increasing concentration of camphor. Nine participants received samples including food grade racemic camphor, with concentrations of 200, 300, 400, 500, 1000, 2000, 4000, 6000 ppm (corresponding to about 400, 600, 800, 1000, 2000, 4000, and 8000 nanograms per sample, respectively).

Participants wore nose clips during evaluation. Each participant sipped the sample, swished it in the mouth for 10 seconds, then spat it out. Each participant then indicated whether irritation was perceived. Between evaluations of each sample, participants rinsed with water and waited for one minute.

Results of the study are listed below in Table 1. The left-most column indicates the participant number of each individual participant. The letter "Y" indicates that the participant felt irritation at the indicated concentration, and the letter "N" indicates that no irritation was felt.

TABLE 1

Determination of irritation threshold of camphor.

| # | 200 ppm | 300 ppm | 400 ppm | 500 ppm | 1000 ppm | 2000 ppm | 4000 ppm | 6000 ppm | Notes |
|---|---|---|---|---|---|---|---|---|---|
| 1 | N | N | N | N | Y | Y | | | Felt slight tingling at 500, burning at 1000 |
| 2 | Y | Y | Y | | | | | | Some burning and stinging at 200, tingling and some burning at 300, burning at 400 |
| 3 | Y | Y | Y | | | | | | Very slight tingling at 200, slight tingling at 300, Stronger tingling no burning at 400 |
| 4 | N | N | N | N | N | Y | Y | Y | Felt slight tingling at 2000, some tingling at 4000, burning at 6000 |
| 5 | N | N | N | N | Y | Y | Y | | Felt some tingling at 1000, stronger tingling at 2000, burning at 4000 |
| 6 | N | N | Y | Y | | | | | Tingling at 300, tingling no burning at 400 |
| 7 | N | N | Y | Y | | | | | Slight tingling and burning at 300 and 400 |
| 8 | N | N | N | Y | | | | | No Burning, slight tingling on edges at 400 |
| 9 | Y | Y | | | | | | | Some burning at 200, stronger burning at 300 |

The study found that the irritation threshold for camphor racemate (D+L) in solution ranges from 200 ppm (slight tingling) to 1000 ppm. Most participants perceived tingling at very low concentrations (200-300 ppm) while a few were sensitive only at higher concentrations (1000-2000 ppm). The mean threshold for producing irritation was 655 ppm for n=9.

Snus Pouches with Camphor

A further study was conducted to determine if camphor affected perceived burning in the mouth of subjects using oral tobacco. Participants were given two snus pouch samples to use simultaneously, one in each side of the mouth. One sample was a control pouch with no camphor added and the other contained various concentrations of camphor (2.3, 6, 12, 23, 46, and 69 nanograms, corresponding to 25, 50, 100, 200, or 300 ppm, based on tobacco weight, respectively).

The hand-made test samples were constructed using unflavored tobacco (12% oven volatiles) to prevent any possible interference of the flavor system with the objective of the study. In preparing the pouches, the camphor was dissolved in 95% ethanol, with the control pouches receiving the ethanol only. Ten (10) microliters of one of the solutions was applied to each sample pouch (5 microliters per side). Using a one (1) microliter pipette, 1 microliter was applied to each corner of the tobacco cavity and the 5th microliter was applied to the center. The same procedure was used for the other side of the pouch. Samples were prepared one day prior to testing and sealed in glass jars overnight. The jars were unsealed each morning of testing to allow volatiles to escape. Unused samples were discarded at the end of each day of testing, and fresh samples prepared for the next day.

The study was carried out as a double-blind, randomized within-subjects two-alternative forced choice (2AFC) design.

In each session, participants were given two (2) test samples (one being a control). Participants were instructed to place one (1) of the two (2) pouches between their gums and upper lip on the left side of the mouth, and place the other pouch between the gums and upper lip on the right side of the mouth. Pouch placement was targeted to the area just below and in front of the cheek bone. The control pouch side was randomly assigned. Participants were instructed to close their mouth and leave the pouches in the locations they were placed. Participants were allowed to squeeze the pouches with their cheeks and wet the pouches with their saliva in order to release additional flavor.

After two (2) minutes, five (5) minutes, and ten (10) minutes of using the samples, participants were asked to indicate which side of the mouth was burning more. Responses were recorded on paper by the experimenter. After participants finished the evaluation, they were instructed to spit the test samples out of their mouths into the provided receptacle. They were provided with water and/or orange juice to cleanse their palates. Following each evaluation, participants were asked to give details regarding where the burning was felt and to provide any open-ended comments regarding their experience, which were recorded on paper by the experimenter. Participants repeated the sensory evaluation procedures an additional six (6) times, with a maximum of two (2) pairs being evaluated each day.

Figure 4B:
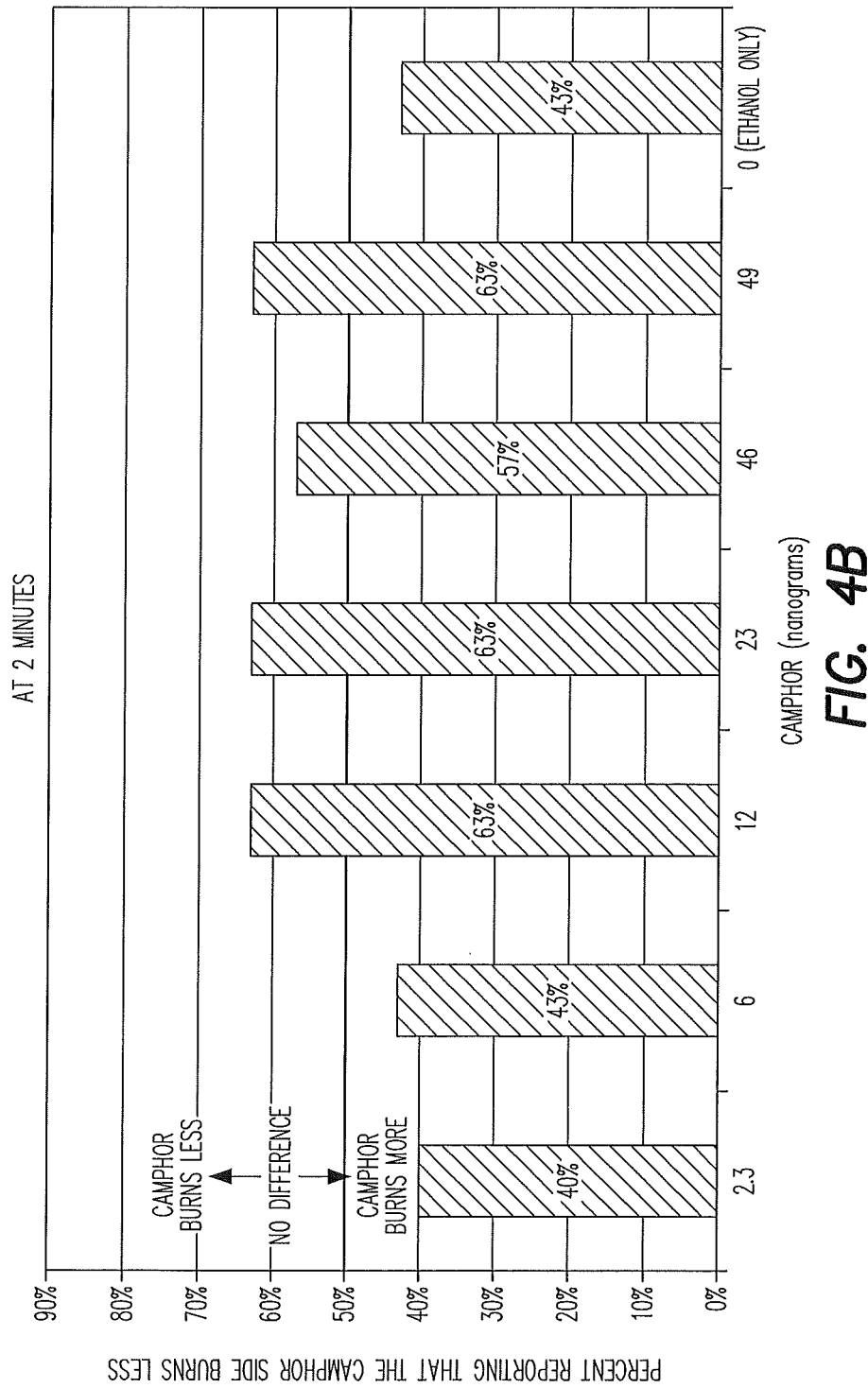
Figure 4D:
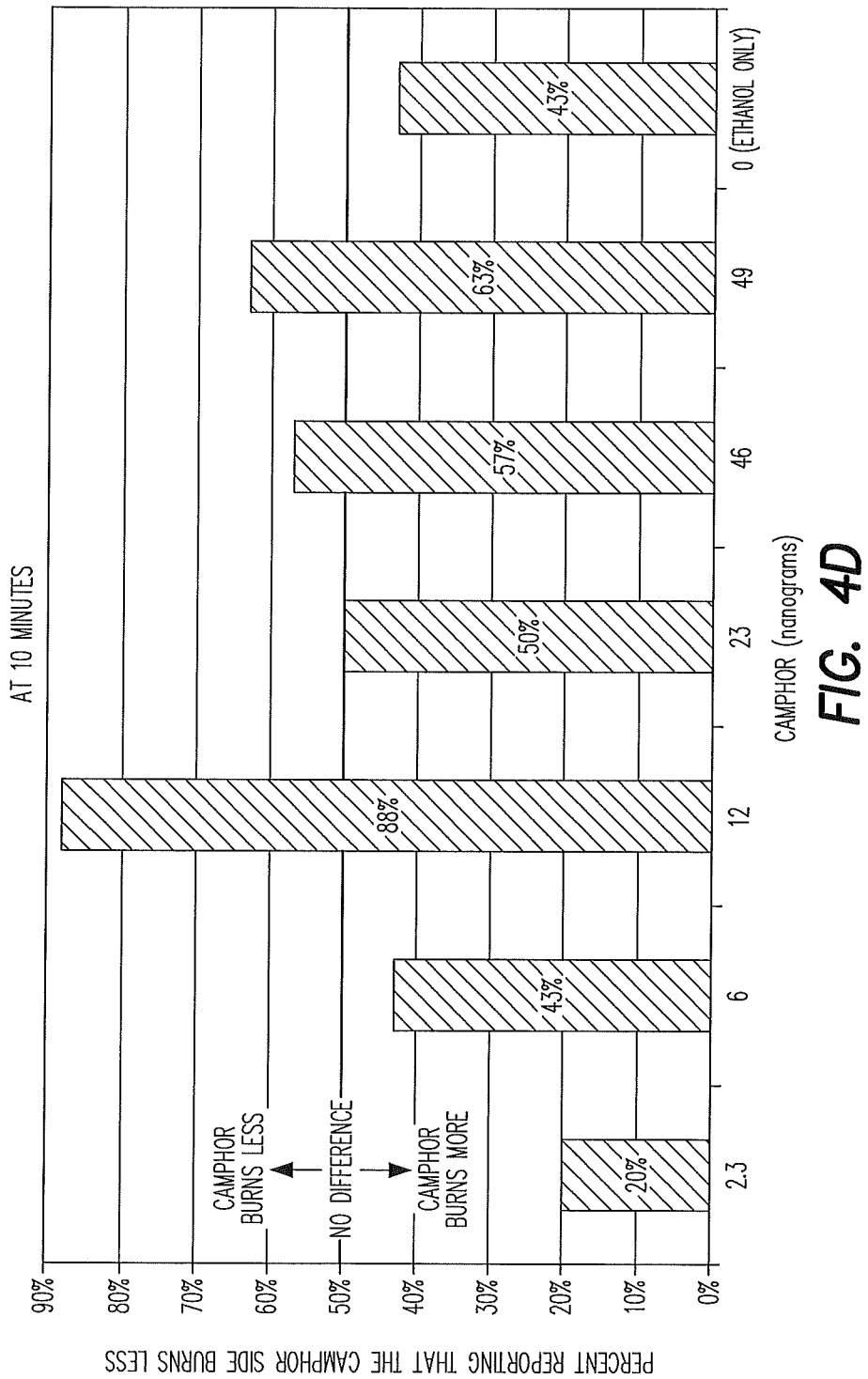
Figure 5A:
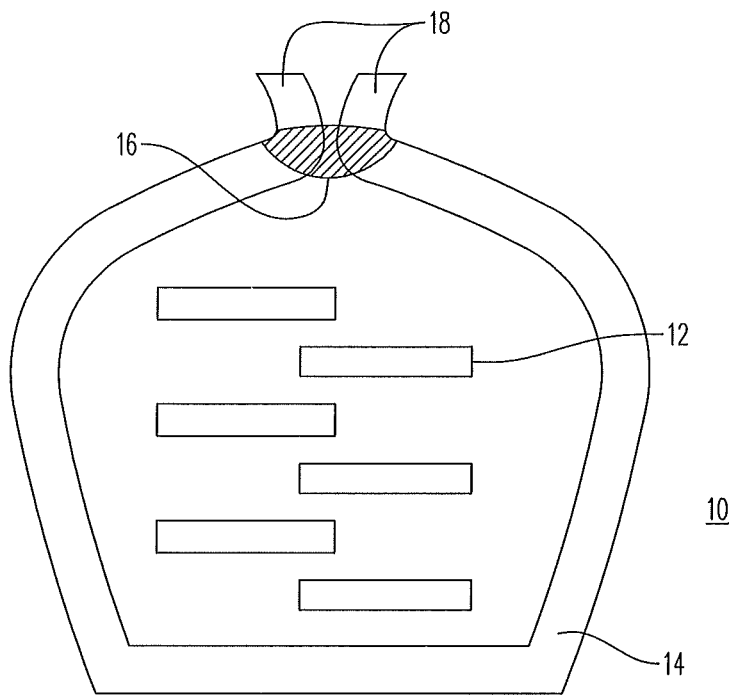
FIG. 5A shows a pouch product with a soft edge and FIG. 5B shows a traditional pouch product.
Figure 5B:
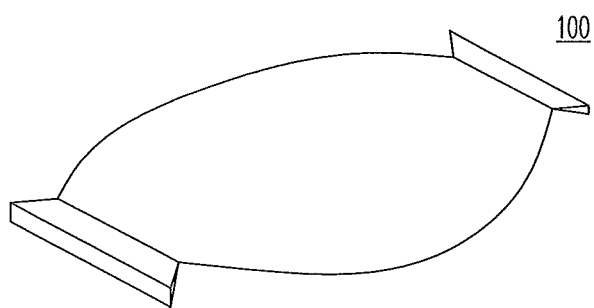

Participants were asked which side of the mouth burned more at 2, 5, and 10 minutes, as seen in FIGS. 4B, C, and D, respectively. FIG. 4A shows results across all times points. The 12 nanogram (corresponding to 50 ppm) quantity of camphor was most effective in reducing oral burning, and the effect was strongest at the 10-min mark.

Other Active Ingredients

Certain ingredients other than camphor are also expected to perform as does camphor, either by acting in the same manner as camphor to inhibit nicotine-mediated activation, and/or by acting a precursor to camphor or another compound acting in the same manner as camphor. Such precursors are expected to be converted to active forms on human consumption (e.g., by metabolic enzymes).

In an embodiment, the role of camphor as described herein is served by at least one compound selected from the group consisting of borneol, isoborneol, bornyl acetate, isobornyl acetate, mono-bornyl succinate, mono-isobornyl succinate, mono-bornyl formate, and mono-isobornyl formate.

A Carrier System for Camphor

The inventors have found a carrier system for camphor which can be advantageously used with a smokeless tobacco product or another product containing nicotine, such as a medicinal nicotine product and/or smoking cessation product. Such a system, when added to, e.g., a smokeless tobacco product, reduces or eliminates sensory irritation including burning, bolus feel in the esophagus, hiccups, and nausea.

The carrier system facilitates transport of camphor to the sensory receptor sites where it exerts its effects, e.g., at TRPA1 and nicotinic acetylcholine receptors. Due to its chemical properties, camphor reaches the receptors more reliably when the carrier system supports the transport of camphor through several epithelial layers to reach the free nerve ending of afferent fibers of spinal or trigeminal (somatosensory) nerves or the vagal nerves.

As described above, camphor was found successful in experimental settings in inhibiting such undesired sensations while dissolved in water/alcohol solutions, for example as applied to smokeless tobacco. However, an improvement was desired in the ability of camphor to exert its positive effects. A number of solvents were investigated and it was found that the most stable effect was achieved when camphor was dissolved in an oily carrier. Using a liquid or a more solid form of an oily carrier would provide these beneficial effects for non-tobacco products as well, such as nicotine chewing gums which are used for smoking cessation. The oily carrier is a non-flavored oily carrier.

In smokeless tobacco products, camphor in a concentration of less than 1300 ppm in mineral oil does not exhibit a sensory effect of its own, such as smell, taste, or extensive cooling.

Figure 6:
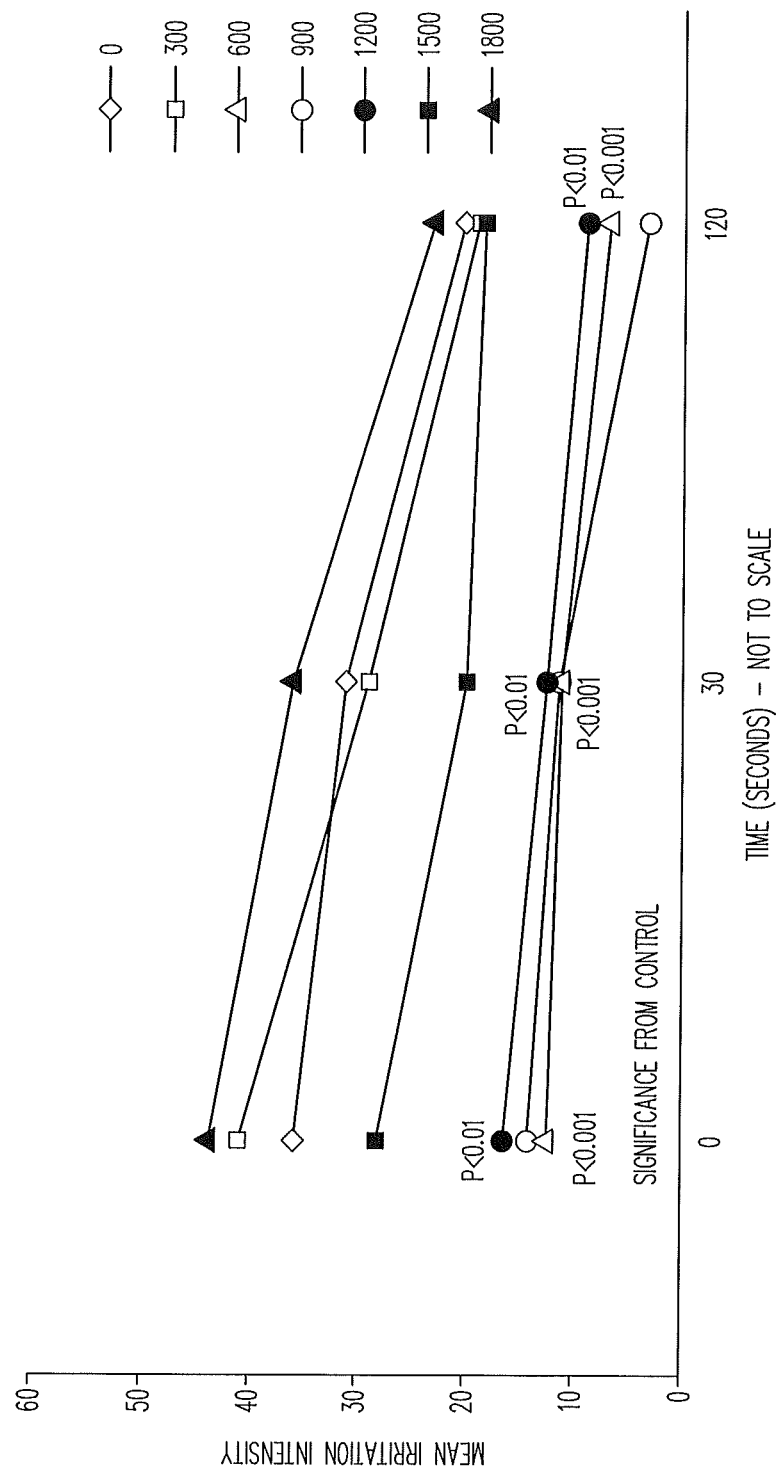
FIG. 6 shows data demonstrating the effect of varying concentrations of camphor on the burning sensation from nicotine using camphor in an oily carrier.

FIG. 6 and Table 1 show data collected demonstrating the effect of varying concentrations of camphor on the burning sensation arising from nicotine. Camphor pretreatment was performed using two taste strips applied bilaterally (blinded, randomized) on the tongues of 18 participants. Test strips had 250 microliters of NEOBEE oil carrier with camphor concentrations of C ranging from 300 ppm to 1800 ppm. Control strips contained 250 microliters of carrier only (NEOBEE Oil). The pretreatment time was about 30 seconds. Participants then removed the taste strips and nicotine strips were placed in treated area. The nicotine was provided in an amount of 730 micrograms in 50 microliters for about 30 seconds. Each nicotine strip was then removed, followed by sensory evaluation of burning immediately, at 30 seconds, and 2 minutes. For sensory evaluation, 2 AFC and sensory irritation intensity ratings were generated.

A repeated measures analysis of variance (ANOVA) model was applied to analyze the data. The model includes terms for study participant, study time and concentration of camphor (see the Table 1). The SAS procedure "PROC MIXED" was used. The p value was for the comparison between each concentration with the control. The chi squared test was used for calculating significance for forced choice values. It was concluded that 600 ppm, 900 ppm and 1200 ppm of camphor demonstrated significant reduction in sensory irritation from nicotine at all time points: immediately, at 30 seconds, and at 120 seconds after nicotine administration.

TABLE 1

| Study time (sec.) | Concentration (ppm) | Difference from control | P value |
|---|---|---|---|
| 0 | 300 | 4.31 | 0.4083 |
| 0 | 600 | −24.03 | <0.0001 |
| 0 | 900 | −22.64 | <0.0001 |
| 0 | 1200 | −19.99 | 0.0010 |
| 0 | 1500 | −8.62 | 0.1500 |
| 0 | 1800 | 7.29 | 0.2235 |
| 30 | 300 | −1.67 | 0.7487 |
| 30 | 600 | −18.00 | 0.0002 |
| 30 | 900 | −19.72 | 0.0002 |
| 30 | 1200 | −14.30 | 0.0024 |
| 30 | 1500 | −11.11 | 0.0641 |
| 30 | 1800 | 5.25 | 0.3797 |
| 120 | 300 | −2.12 | 0.6823 |
| 120 | 600 | −13.80 | 0.0086 |
| 120 | 900 | −17.69 | 0.0008 |
| 120 | 1200 | −11.93 | 0.0471 |
| 120 | 1500 | −2.38 | 0.6901 |
| 120 | 1800 | 2.16 | 0.7172 |

Without wishing to be bound by theory, it is believed that the reduction in irritation was due to camphor-mediated reduction in activation of nicotinic acetylcholine receptors and/or of vanilloid receptors such as TRPV1 and/or TRPA1 receptors. The criticality of camphor in the range of about 600 to 1200 ppm was unexpected.

For medicinal nicotine preparations, such as smoking cessation products, it can be anticipated that patients' compliance will be substantially increased because of the reduction and elimination of unwanted side effects, thus potentially increasing the quitting success rates.

In an embodiment, a portion of a product includes a quantity of camphor equivalent to or greater than that provided in 600 ppm to 1200 ppm of camphor in 250 microliters.

The non-flavored oily carrier is a hydrophobic carrier substantially lacking in flavor. Examples thereof include mineral oil and vegetable oil, and their derivatives, as well as waxes.

Smokeless Tobacco

As described herein, portions of smokeless tobacco include both pouched tobacco (sometimes called snus pouches) and pouchless portions that are free of a fabric and/or paper wrapper and comprise orally enjoyable tobacco that has been molded or divided into individual servings prior to use, such that the pre-portioned tobacco can be placed in a user's mouth without the need for the user to determine an amount to use. Pre-portioned, pouchless products of plant material, such as tobacco, are described in commonly-owned U.S. Patent Application Publication Nos. 2008/0202533, 2009/0038631, and 2009/0301505, each of which is incorporated by reference. Pouched portions are described in, e.g., U.S. Patent Application Publication Nos. 2007/0012328 and 2007/0261707, each of which is incorporated by reference.

Preferably, the portion has a generally rectangular or elliptical shape. Other preferred shapes for the pouch include any shape selected from the group consisting of polygons, squares, rectangles, circles, ovals, heart, star, half-moon, crescent, leaf shapes, and combinations thereof.

In a preferred embodiment, the portion is sized and configured to fit inside the mouth, between a user's cheek and gum. Preferably, the pouch takes a generally rectangular shape and is about 20 mm to about 35 mm long, about 10 mm to about 20 mm wide and about 3 mm to about 6 mm thick.

The camphor in an oily carrier may be applied to the exterior of a portion, either by itself or as part of a coating on the portion. Alternately, or in addition, the camphor may be in an interior region of the portion.

Medicinal Nicotine Products

The product may be provided in a variety of forms. In an embodiment, the product is an edible product. An edible product can take the form of a tablet, lozenge, stick, chewable gum, spongy material, foam, cream, pellet, fiber, pill, capsule, pouched products, or combinations of these. Other examples of edible products include such chewable or non-chewable edible forms as tablets, gums, chocolates, flavored sponges, flavor strips, and the like.

In another embodiment, a medicinal nicotine product or preparation is provided in a spray form, i.e., a sprayable product that allows a user to spray the camphor and oily carrier into the mouth. If the product is to be administered in a spray form, the packaging preferably comprises an inhaler, such as a metered inhaler.

While the foregoing has been described in detail with reference to specific embodiments thereof, it will be apparent to one skilled in the art that various changes and modifications may be made, and equivalents thereof employed, without departing from the scope of the claims.

What is claimed is:

1. A method of making a smokeless tobacco product comprising:
   combining nicotine and camphor dissolved in a non-flavored oily carrier, wherein the camphor is present in the product in a concentration ranging from about 600 ppm to about 1300 ppm,
   wherein the nicotine is provided in a portion of smokeless tobacco; and
   wherein the product comprises a pouch comprising the smokeless tobacco enclosed in a water-permeable wrapper.

2. The method of claim 1, wherein:
   (a) the camphor is in a coating on the wrapper of the pouch; and/or
   (b) the pouch has a soft edge.

3. The method of claim 1, wherein the camphor is present in an amount effective to reduce or eliminate sensory irritation arising from consumption of the nicotine.

4. The method of claim 1, wherein the camphor is present in the product in a concentration ranging from 600 ppm to 1200 ppm.

* * * * *